US008153148B2

(12) United States Patent
Maspero et al.

(10) Patent No.: US 8,153,148 B2
(45) Date of Patent: *Apr. 10, 2012

(54) POROUS BIOCOMPATIBLE IMPLANT MATERIAL AND METHOD FOR ITS FABRICATION

(75) Inventors: Fabrizio Alessandro Maspero, Zurich (CH); Kurt Ruffieux, Schlieren (CH)

(73) Assignee: Degradable Solutions AG, Schlieren (CH)

( * ) Notice: Subject to any disclaimer, the term of this patent is extended or adjusted under 35 U.S.C. 154(b) by 1545 days.

This patent is subject to a terminal disclaimer.

(21) Appl. No.: 10/507,094

(22) PCT Filed: Feb. 22, 2003

(86) PCT No.: PCT/EP03/01812
§ 371 (c)(1),
(2), (4) Date: Sep. 3, 2004

(87) PCT Pub. No.: WO03/075975
PCT Pub. Date: Sep. 18, 2003

(65) Prior Publication Data
US 2005/0209704 A1 Sep. 22, 2005

(30) Foreign Application Priority Data
Mar. 14, 2002 (EP) .................................. 02005844

(51) Int. Cl.
*A61F 2/08* (2006.01)
(52) U.S. Cl. ..................................................... 424/426
(58) Field of Classification Search .................. 424/422, 424/423, 426; 623/23.5, 23.51; 264/100
See application file for complete search history.

(56) References Cited

U.S. PATENT DOCUMENTS

| 3,918,968 A * | 11/1975 | Kukla et al. ..................... 430/31 |
| 3,919,773 A | 11/1975 | Freeman et al. |
| 4,237,559 A | 12/1980 | Borom |
| 4,429,691 A * | 2/1984 | Niwa et al. ........................ 606/77 |
| 4,430,760 A | 2/1984 | Smestad |
| 4,610,692 A | 9/1986 | Eitenmuller et al. |
| 4,645,503 A * | 2/1987 | Lin et al. ...................... 623/23.58 |
| 4,685,883 A | 8/1987 | Jernberg |
| 4,938,763 A | 7/1990 | Dunn et al. |
| 5,077,049 A | 12/1991 | Dunn et al. |
| 5,278,201 A | 1/1994 | Dunn et al. |
| 5,324,520 A | 6/1994 | Dunn et al. |
| 5,338,772 A * | 8/1994 | Bauer et al. ..................... 523/115 |
| 5,340,849 A | 8/1994 | Dunn et al. |
| 5,433,751 A | 7/1995 | Li et al. |
| 5,487,897 A | 1/1996 | Polson et al. |
| 5,501,687 A | 3/1996 | Willert et al. |
| 5,531,791 A | 7/1996 | Wolfinbarger |
| 5,552,454 A * | 9/1996 | Kretschmann et al. ........ 523/113 |
| 5,626,861 A | 5/1997 | Laurencin et al. |
| 5,648,097 A * | 7/1997 | Nuwayser ....................... 424/489 |
| 5,681,873 A | 10/1997 | Norton et al. |
| 5,702,716 A | 12/1997 | Dunn et al. |
| 5,725,491 A | 3/1998 | Tipton et al. |
| 5,733,950 A | 3/1998 | Dunn et al. |
| 5,741,329 A | 4/1998 | Agrawal et al. |
| 5,866,155 A | 2/1999 | Laurencin et al. |
| 5,962,006 A | 10/1999 | Southard et al. |
| 6,120,789 A | 9/2000 | Dunn |
| 6,132,214 A | 10/2000 | Suhonen et al. |
| 6,143,314 A | 11/2000 | Chandrashekar et al. |
| 6,201,039 B1 | 3/2001 | Brown et al. |
| 6,203,574 B1 | 3/2001 | Kawamura |
| 6,261,583 B1 | 7/2001 | Dunn et al. |
| 6,294,187 B1 | 9/2001 | Boyce et al. |
| 6,332,779 B1 | 12/2001 | Boyce et al. |
| 6,340,477 B1 | 1/2002 | Anderson |
| 6,344,496 B1 | 2/2002 | Niederauer et al. |
| 6,432,438 B1 | 8/2002 | Shukla |
| 6,455,024 B1 * | 9/2002 | Glajch et al. ................. 424/1.33 |
| 6,461,631 B1 | 10/2002 | Dunn et al. |
| 6,616,698 B2 | 9/2003 | Scarborough |
| 6,696,073 B2 | 2/2004 | Boyce et al. |
| 6,770,695 B2 | 8/2004 | Ricci et al. |
| 6,869,445 B1 * | 3/2005 | Johnson ...................... 623/17.11 |
| 7,001,551 B2 | 2/2006 | Meredith |
| 7,241,316 B2 | 7/2007 | Evans et al. |
| 7,270,813 B2 | 9/2007 | Shimp et al. |
| 7,731,756 B2 | 6/2010 | Maspero et al. |
| 2001/0014831 A1 | 8/2001 | Scarborough |
| 2002/0016636 A1 * | 2/2002 | Ricci et al. ................. 623/23.51 |
| 2002/0028511 A1 | 3/2002 | de Bruijn et al. |
| 2003/0009235 A1 | 1/2003 | Manrique et al. |
| 2003/0026770 A1 | 2/2003 | Szymaitis |
| 2003/0055512 A1 | 3/2003 | Genin et al. |
| 2003/0104029 A1 | 6/2003 | Pirhonen et al. |
| 2005/0249773 A1 | 11/2005 | Maspero et al. |
| 2005/0251266 A1 | 11/2005 | Maspero et al. |

FOREIGN PATENT DOCUMENTS

DE 3106445 A 11/1982
(Continued)

OTHER PUBLICATIONS

H. H. Lu, *3-D Porous Polymer-Bioactive Glass Composite Promotes Collagen Synthesis and Mineralization of Human Osteoblast-like Cells*, Sixth World Biomaterials Congress Transactions, 2000 Society for Biomaterials, p. 972. Robert C. Thomson et al., "Hydroxyapatite fiber reinforced poly(α-hydroxy ester) foams for bone regeneration", Biomaterials, Elsevier Science Publishers BV, Barking, GB, vol. 19, No. 21, Nov. 1998, pp. 1935-1943.
David J. Mooney et al., "Novel approach to fabricate porous sponges of poly(D,L-lactic-co-glycolic acid) without the use of organic solvents", Biomaterials, Elsevier Science Publishers BV, Barking, GB, vol. 17, No. 14, Jul. 1996, pp. 1417-1422.

(Continued)

*Primary Examiner* — Carlos Azpuru
(74) *Attorney, Agent, or Firm* — Buchanan Ingersoll & Rooney PC (57) ABSTRACT

A biocompatible and biodegradable implant for a cavity in a bone of a living organism is made of biocompatible and biodegradable granules. The biocompatible and biodegradable granules are provided with a coating, which includes at least one layer of a biocompatible and biodegradable polymer. The biocompatible and biodegradable implants are obtained by fusing together the polymer-coated granules through polymer-linkage of the polymer coatings of neighboring granules.

31 Claims, 2 Drawing Sheets

FOREIGN PATENT DOCUMENTS

| | | |
|---|---|---|
| DE | 3134728 A | 3/1983 |
| EP | 0 950 403 A2 | 10/1999 |
| EP | 1 344 538 A1 | 9/2003 |
| WO | WO 87/05521 A1 | 9/1987 |
| WO | WO 90/01342 A1 | 2/1990 |
| WO | WO 92/00718 A1 | 1/1992 |
| WO | WO 95/27481 A1 | 10/1995 |
| WO | WO 95/28124 A1 | 10/1995 |
| WO | WO 96/21427 A1 | 7/1996 |
| WO | WO 00/01760 A1 | 1/2000 |
| WO | WO 00/06117 A1 | 2/2000 |
| WO | WO 00/35510 A1 | 6/2000 |
| WO | WO 00/50104 A1 * | 8/2000 |
| WO | WO 03/004764 A1 | 1/2003 |
| WO | WO 03/047646 A1 | 6/2003 |

OTHER PUBLICATIONS

Definition of "Conditioner" (http://www.thefreedictionary.com/conditioner), citing The American Heritage Dictionary of the English Language, Fourth Edition, 2000, Houghton Mifflin Company, Updated 2009.

Maspero et al., Copending U.S. Appl. No. 10/840,041, filed May 6, 2004, entitled, "Biocompatible Bone Implant Compositions and Methods for Repairing a Bone Defect".

Maspero et al., Copending U.S. Appl. No. 11/121,831, filed May 4, 2004, entitled, "Biocompatible Bone Implant Compositions and Methods for Repairing a Bone Defect".

* cited by examiner

POROUS BIOCOMPATIBLE IMPLANT MATERIAL AND METHOD FOR ITS FABRICATION

The present invention concerns a biocompatible and biodegradable implant for implantation and/or insertion into cavities of a living organism such as bone defects or extraction wounds and methods for its fabrication.

INTRODUCTION AND BACKGROUND OF THE INVENTION

Bone defects can be treated by the implantation of an autograft, an allograft, or a xenograft in the healing site. However, these biological implants suffer of many drawbacks, among them, for example, shortage of donor tissue, bacterial and viral contamination, etc. Biocompatible synthetic implants generally present less osteoconductive and osteoinductive effects than biological grafts. But they are usually save and can be manufactured in a reproducible manner.

In dental treatment, for example, the extraction of a tooth leaves an open wound that might be contaminated by bacteria. Moreover, it is a known problem that due to the absence of the tooth, alveolar bone spontaneously undergoes remodeling, leading to its atrophy. Such atrophy may then cause many complications for subsequent reconstruction. In order to prevent this process, it has been suggested in the prior art (U.S. Pat. No. 6,132,214) to implant into the extraction site a biodegradable implant, which is an exact copy of the extracted tooth. Although such implants lead to promising results, the bone in-grow in the alveolar site is relatively low, in particular in the early stage of the healing process. The use of poly($\alpha$-hydroxy acids), such as, for example polyglycolide, polylactide, or co-polymers thereof, leads to a massive release of acidic products in the environment of the implant during its degradation. This acidification of the environment may then even provoke tissue necrosis.

While the problems of the prior art have been described with reference to dental problems it will be appreciated by those skilled in the art that implants are also used as treatments for other skeleton parts. If, for example, a part of the skeleton is stricken by a tumor, the area stricken by the tumor may be removed and replaced by an implant. In that case with the implants known from the prior art similar problems as those described with respect to dental treatments may arise.

Other known implant systems and methods include, for example U.S. Pat. No. 5,741,329. In this reference, it is suggested to control the changes of the pH value in the vicinity of biodegradable implants. Thus, during the degradation of the implant the pH value is effectively maintained between 6 and 8 by incorporating a basic salt, preferably calcium carbonate or sodium bicarbonate into a polymeric matrix, preferably poly(lactide-co-glycolide) with a lactide to glycolide molar ratio of 50/50. An amount of about 5% to about 30% of ceramic particles is dispersed in the polymer. The resultant porous implants are only poorly interconnected and have only poor mechanical stability.

In DE-A-31 06 445 a combination of osteoconductive bioceramics with biodegradable polymers is proposed in order to prepare osteoconductive biodegradable implants. Porous tricalcium phosphate ceramics are impregnated with a therapeutically active sub stance, which is disposed in the pores of the ceramics body. For controlling the release of the therapeutically active substance the sintered bioceramic is then coated with a polymer film (e.g. polydextran). In U.S. Pat. No. 4,610,692 it is suggested to impregnate a porous sintered tricalcium phosphate body with therapeutically active substances, such as antibiotics (e.g. gentamicin). and/or disinfecting substances (e.g. polyvinyl pyrrolidone iodine). The release of these substances is controlled by coating the sintered bioceramic porous body with a polymer film (e.g. polymethacrylate, polylactide, polydextran).

From the prior art there are already known open porous implants which are made from an aggregation of granules. In U.S. Pat. No. 5,626,861, a polymer matrix consisting preferably of 50/50 polylactide/polyglycolide copolymer is described, which is reinforced with particulate hydroxyapatite. This combination of materials of materials is supposed to permit to maintain the integrity of the implant as the degradation proceeds. Also the osteoconductive potential is supposedly increased. In the manufacture of the implant particulate hydroxyapatite having an average particle size of about 10-100 μm, and inert leachable particles (e.g. NaCl of a particle size of about 100-250 μm) are suspended in a PLGA solvent solution. The polymer solvent solution is emulsified and cast into any appropriate mold. As the solvent is evaporated from the salt, ceramics and polymer mixture, the dried material retains the shape of the mold. The salt particles within the implant are then leached out by immersion in water. By this method pores having a diameter of about 100-250 μm are left in the implant. The major drawback of this method is the necessity of a complete removal of the organic solvent, which takes time and requires costly analysis before the implant may be applied to the patient in order to treat bone defects.

In U.S. Pat. No. 5,866,155 a method for the manufacture of three-dimensional macroporous polymer matrices for bone graft is suggested. For that purpose calcium phosphate based materials are added to polymer microspheres in order to produce flexible matrices for bone replacement or tissue engineering. In one embodiment a sintered microsphere matrice is prepared. A mixture containing degradable polymer microspheres, calcium phosphate based materials and porogen particles (NaCl) is cast in a mold, compressed and sintered such, that the microspheres of the cast mixture bond to each other after heating over their glass transition temperature. After removal from the mold and cooling, the porogen is leached out in order to produce a matrice for use in bone replacement. In a second embodiment it is described that the microspheres a bonded together by using an organic solvent. After removal of the solvent and leaching out of the porogen material three-dimensional structures are obtained for bone replacement. A still further alternative method consists in the preparation of gel-like polymer microspheres, having sticky surfaces. Calcium-phosphate particles are then added to the sticky microspheres. The mixture is stirred, cast in a mold and dried in order to obtain the desired open porous structure.

Lu et al. in "3D Porous Polymer Bioactive Glass Composite Promotes Collagen Synthesis and Mineralization of Human Osteoblast-like Cells", Sixth World Biomaterials Congress Transactions, Hawaii, (2000), p: 972 describe a method to prepare 3-D constructs made of Bioglass® 45S5 and poly(lactide-co-glycolide). The method consists of the dissolution of the polymer in a methylene chloride and the addition of Bioglass granules having a size of less than 40 μm, to the solution. The mixture is then poured into a 1% polyvinyl alcohol solution and the spheres are allowed to harden. 3-D constructs are made by heating the microspheres in a mold at 70° C. for 20 hours. The method suffers the disadvantage that it is very difficult to control the degree of deposition of the polymer on the surface of the bioglass granules. An aggregation of the granules is also difficult to avoid. A heat treatment of the granules generally leads to problems, in particular if highly volatile and/or thermolabile biologically active substances, such as, for example, growth factors, are to be added to the granules.

In U.S. Pat. No. 6,203,574 it is suggested to bond ceramic granules with each other using a biodegradable substance. By the suggested method an interconnecting open porous structure is supposed to be obtained. Hydroxyapatite particles of sizes from 100-300 μm are heated to 200° C., while polylactide particles having a particle size smaller than 210 μm are heated to 100° C. The hydroxyapatite particles are then added to the polylactide particles. The mixture is intimately shaken in order to obtain a homogeneous mixture of particles. By this method the polylactide adheres to the surface of the hydroxyapatite particles. Thereafter, a mixture of polylactide particles containing fine hydroxyapatite and polylactide granules with a size of 210-420 μm is added to the coated large hydroxyapatite particles. The resulting mixture is poured into a mold and heated to 195° C. After cooling a molded open porous implant is obtained. However, this method suffers a number of drawback. The particles are bonded together in a heating process, which excludes the incorporation of thermally labile osteoinductive substances such as growth factors or other proteins. Antibiotics can also be altered and even destroyed by the necessary elevated temperatures. Although the polylactide particles are supposed to adhere to the surface of the ceramic particles they can also adhere to each other. Thus, aggregates of polylactide are formed. This can lead to the formation of inhomogeneous implants. The suggested method does not allow the control of the thickness and homogeneity of the coating of the ceramic particles. Thus, the suggested system may not be optimal for a controlled delivery of pharmaceutically active substances. Moreover, the suggested method is incompatible with the desire to use as little polylactide as possible for the production of implants.

OBJECTS AND SUMMARY OF THE INVENTION

It is an object of the present invention to provide a biocompatible and biodegradable implant, which overcomes the aforementioned problems associated with materials and methods of implantation and/or insertion into bone cavities or extraction wounds. A biocompatible and biodegradable implant is to be provided which upon insertion/implantation assists in the reduction of a loss of bone volume. It is a further object of the present invention to provide an implant which may be assembled and shaped easily in the desired manner to a defect-analogous implant in order to avoid hollow spaces between the implant and the sidewalls of the cavity. There is to be provided an implant having an open interconnected macro porosity, which allows tissue in-growth. The properties of the biocompatible implant shall be such, that it also may be used for reduction of bacterial growth and infection in a bone wound and the like. It is still a further object of the invention to provide a method for a fast and comparably simple and cost effective fabrication of the biocompatible and biodegradable implant according to the invention.

According to the invention a biocompatible and biodegradable implant for the filling of a cavity in a living organism such as, for example, a bone defect, is suggested which is made of a number of biocompatible and biodegradable granules made of materials selected from the group consisting of biopolymers, bioglasses, bioceramics preferably calcium sulfate, calcium phosphate such as monocalcium phosphate monohydrate, monocalcium phosphate anhydrous, dicalcium phosphate dihydrate, dicalcium phosphate anhydrous, tetracalcium phosphate, calcium orthophosphate phosphate, α-tricalcium phosphate, β-tricalcium phosphate, apatite such as hydroxyapatite, or a mixture thereof. The biocompatible and biodegradable granules are provided with a coating, which comprises at least one layer of a biocompatible and biodegradable polymer. The biocompatible and biodegradable polymer-coating is selected from the group consisting of poly(α-hydroxyesters), poly(orthoesters), polyanhydrides, poly(phosphazenes), poly(propylene fumarate), poly(ester amides), poly(ethylene fumarate), polylactide, polyglycolide, polycaprolactone, poly(glycolide-co-trimethylene carbonate), polydioxanone, co-polymers thereof or blend of those polymers. The biocompatible and biodegradable implants are obtained by fusing together the polymer-coated granules through polymer-linkage of the polymer coatings of neighboring granules.

By special selection of the biocompatible and biodegradable materials for the granules and their coatings, the growth and the proliferation of osteoblast-like cells may be supported during the degradation of the implant, which is finally replaced by newly formed bone tissue. The implant may in certain cases also prevent the erosion of the bone tissue surrounding the bone defect to be healed.

The fusing process is carried out such, that implants having an open interconnected porosity with macropores having average diameter from about 100 μm to about 500 μm, preferably about 200 μm to about 300 μm is achieved.

The fusing of the polymer-coated granules to a biocompatible and biodegradable implant is carried out with biocompatible and biodegradable granules having micropores with average diameters of about larger than 0 to about 10 μm. The employed process is selected such, that in the implant the microporosity remains and/or macropores are formed having average diameters of about more than 10 μm to about 500 μm, preferably about 100 μm to about 300 μm.

It is to be noted that only the uncoated biocompatible and biodegradable granules have the claimed porosity; once the granules are coated the porosity is practically not recognizable any more from the outside. Granules made of bioceramics, which have been sintered very densely, do not have a considerable microporosity at all. The porosity of the granular material and/or the implants provides an even larger surface area. In addition the pores may be filled, e.g., with an antibiotic substance, with growth factors and like biologically active substances. Thus, the biocompatible and biodegradable implants, when implanted into a cavity or extraction wound not only fill the cavity, but permit the controlled release of biologically active substances. For example, the substance within the pores may be selected such that bacterial growth, fungal growth and the like more are hindered.

Preferably granules are selected, which have an equivalent-diameter of about 350 μm to about 2000 μm, preferably 500 μm to 1000 μm. Granules of the selected equivalent diameters are easily handled and readily further processed.

While the term equivalent-diameter indicates that the biocompatible and biodegradable granules may be of irregular shape, it is of advantage when it is provided with a regular shape. Preferably it has a generally spherical shape. Due to its homogeneous structure the spherical shape of the granular material allows a better handling and an easier estimation of the required quantity of granular material in order to fill a known volume of a cavity.

The biocompatible and biodegradable granules are preferably formed from a powdery base material, said powdery base material having an equivalent diameter of about 0.1 μm-about 10 μm and granules being formed by an additive granulation in a granulator. This method for forming granules is well approved and allows a reproducible formation of granular material having the desired equivalent diameters with only small deviating fractions.

In an alternative embodiment of the invention the biocompatible and biodegradable granules may be hollow instead of being solid granules. The use of hollow granules reduces the amount of implanted material and allows a better in situ integration. In a further advantageous embodiment, the granules may comprise at least opening in the wall enclosing the interior hollow space, which opening in the wall is larger than micropores in the wall, and being preferably of macroscopic size. By providing the hollow biocompatible and biodegradable granules with an opening in the granule wall the possibility of a tissue in-growth into the biocompatible and biodegradable implants is enhanced. The hole with an opening in the granule wall may be produced from slurry consisting of the biocompatible material, water and an adhesive (Wintermantel et al. 1996). Droplets of the slurry are brought onto a heated plate. The water in the slurry droplet boils and evaporates instantaneously out of the droplets leaving an evaporation crater in the droplet wall. When the droplets are cooled off, hollow granules having an opening in the granule wall are formed.

The biocompatible and biodegradable coating has a thickness of 2 µm to 300 µm, preferably about 5 µm to about 20 µm. The mechanical stability of an implant made of coated granules depends on the thickness and the homogeneity of the coating. By an insufficient coating thickness the granules cannot stick together in the required extent. On the other hand, large amounts of coating materials can lead to the decrease of the pH-value below pH 7.4 in the vicinity of the implant during its degradation. Therefore, the optimal thickness of the biocompatible coating is a result of a compromise between implant stability and the amount of material, which will degrade. The preferred coating thickness of the granules may also be expressed as a weight fraction of about 4% to about 15% coating materials of the total weight of the implant. The biocompatible coating is made of a biodegradable polymer. Thus, it is ensured, that after a specified and defined time period the coated granular material may degrade or be resorbed or dissolve within the cavity without any residues.

The coating of the biocompatible and biodegradable granules may comprise one or more layers of varying average thickness. At least the outmost coating layer is made of a biodegradable material. This embodiment of the invention allows providing the biocompatible and biodegradable granules with several coatings for specific purposes. The outmost biodegradable coating may be selected in accordance with a certain desired delay in degradability. Thus, the coating layer underneath is only exposed after a certain desired time period has expired. This, for example, allows a retarded delivery of a bioactive substance. Thus, the biocompatible and biodegradable granules may be coated with different coatings, which each is biodegradable and displays a specific effect.

In a further embodiment of the invention a biologically active substance is integrated into the biocompatible and biodegradable granules and/or into the coating, and/or forming a coating layer itself. Thus, a controlled delivery of the biologically active substance is enabled. The amount of the biologically active substance may easily be defined by controlling the coating process, for example. By integrating biologically active substance into a submerged coating layer or into the granular material itself, a controlled retarded release of the biologically active substance may be accomplished.

The biocompatible and biodegradable implants are easily formed from biocompatible and biodegradable granules. This implant comprises a number of coated biocompatible and biodegradable granules and may be shaped in any required manner. Thus, the biocompatible and biodegradable granules form the prerequisites for temporary implants, which may very easily be shaped to form an exact match of a freshly created cavity or extraction wound. The porosity of the implants is well controllable by the applied method for fusing of the granules. The coated granules are selected from solid granules, porous granules, hollow granules, hollow granules with at least one opening in the granule wall, or mixtures thereof.

It may be advantageous to provide a biocompatible and biodegradable implants, which comprises in addition non-coated biocompatible granules made of a biocompatible and biodegradable material selected from the group consisting of one of biopolymers, bioglasses, bioceramics preferably calcium sulfate, calcium phosphate such as monocalcium phosphate monohydrate, monocalcium phosphate anhydrous, dicalcium phosphate dihydrate, dicalcium phosphate anhydrous, tetracalcium phosphate, calcium orthophosphate phosphate, α-tricalcium phosphate, β-tricalcium phosphate, apatite such as hydroxyapatite, or a mixture thereof, and said granules being free from any coatings and selected from solid granules, porous granules, hollow granules, hollow granules with at least one opening in the granule wall, and mixtures thereof. The coated and uncoated granules are thoroughly mixed such, that they are safely fused together by the preferred method of production and still hare the required stability. By providing a mixture of coated and non-coated granules for the prod of the biocompatible and biodegradable implants, the amount of coating materials, which must degrade, may be further reduced.

The biocompatible and biodegradable implant may consist of one type of biocompatible and biodegradable granules only. In a preferred embodiment of the invention, the biocompatible and biodegradable implant is made of two or more kinds of coated granules. The term different includes biocompatible and biodegradable granules having different sizes. The coated granules are distinct from each other and may consist of different biocompatible materials and/or comprise polymer-coatings, which are distinct from each other. Thus, an implant may be "designed" not only as an ideal match for a bone cavity or an extraction wound but also in accordance with further specific requirements, such as, for example, stability, resorbability and/or solubility of the implant.

In a preferred embodiment the biocompatible and biodegradable implant is obtained from biocompatible and biodegradable granules which are fused together within a mold in a pressurized $CO_2$ atmosphere. The $CO_2$ atmosphere acts as a slight solvent with respect to the polymer-coated granules and enhances the linkage of the granules with each other. The produced biocompatible and biodegradable implants preferably comprise macropores in between the fused together granules. The macropores may be interconnected and have average sizes from about 100 µm to about 500 µm, preferably about 200 µm to about 300 µm. The macropores serve to enhance the in-growth of tissue into the implant and thus allow a faster regeneration of the healing site.

A preferred field of use for the biocompatible and biodegradable implant according to the invention is the use as a temporary replacement for an extracted tooth root or the like. Fusing of the individual polymer-coated granules to a making implant may be accomplished very easily and very fast on-site from prefabricated biocompatible and biodegradable granules.

The biocompatible and biodegradable granules may be spray-coated, preferably in a fluid bed machine, or immersion-coated with the desired biocompatible polymer(s). Both methods lead to the biocompatible and biodegradable granules having the required properties. The spray coating process in a fluid bed machine is preferred though, because it allows the fabrication of a great number of practically identical polymer-coated biocompatible and biodegradable granules in a very fast and economic manner. The technique is well proven and allows an easy control of the thickness of the coating layer(s) and the fabrication of biocompatible and biodegradable granules having multiple coating layers, which are distinct from each other. The coating in fluidized bed machine results in a homogenous and continuous coating, which offers a barrier against bacterial contamination of the granules or of implants made therefrom. During the coating process, the granules do not adhere to each other, thus avoiding the formation of undesirable aggregates which might lead to highly inhomogeneous size distributions and coating thickness. The coated granules retain their excellent free-flow properties, which is necessary for an eventual further processing. Due to the homogeneity of the coating only a low amount of coating material, in particular PLGA, is required for the further consolidation of an implant. Thus, the risks of inflammation or tissue necrosis due to a massive release of acidic products in the environment of an implant during its degradation are significantly reduced. An integration of biologically active substances into the coating film(s) may be well controlled by the coating in a fluid bed machine. Thus, each granules is loaded with the same amount of the biologically active substance. The thickness of the coating is well controlled in the process. Therefore, even the release of an integrated biologically active substance is predictable and well controlled.

Biocompatible and biodegradable implants are made from coated granules of a biocompatible and biodegradable material. They may also comprise uncoated granules. The granules are preferably fused together in a mold having a cavity corresponding to the required shape. After removal from the mold the implants need not be finished but may be directly inserted into a bone cavity or an extraction wound. However, due to the relatively high stability of the implants, they may even be further finished, such as, for example, by cutting away portions of the implant, if the need arises.

The fusing together of the biocompatible and biodegradable granules may also be accomplished by heat treatment, or by exposure to a solvent. The selected method depends on the type of coating and may employ even combinations of the different kinds of mechanical, physical and chemical processes. In a method the biocompatible and biodegradable granules are fused together within a mold having the desired mold cavity by subjecting them to a pressurized $CO_2$ atmosphere for a time span of at least about 3 seconds, typically about 3 seconds to about 180 seconds. The $CO_2$ atmosphere acts as a slight solvent with respect to the polymer-coated granules and enhances the linkage of the granules with each other. The pressure of the $CO_2$ atmosphere ranges from about 20 bar to about 200 bar, preferably about 50 bar. At these pressures a reliable bondage of the granules to each other is achieved while at the same time avoiding a damage of the individual biocompatible and biodegradable granules. The bonding of the granules in a $CO_2$ atmosphere has the advantage that the produced biocompatible and biodegradable implant does not require any purification step prior to implantation.

In an alternative method the fusing together of the biocompatible and biodegradable granules is accomplished by heat treatment. The fusion of the coated granules is achieved at elevated temperatures of about 70° C. to about 220° C., preferably about 75° C. to about 90° C. The heat treatment lasts for a time span of at least about 10 seconds, typically about 10 seconds to about 5 minutes.

The incorporation of growth factors into a biocompatible and biodegradable implant can also be achieved very simply by mixing loaded microspheres with the biocompatible and biodegradable coated granules. This allows manufacturing the coated granules under non-aseptic conditions with subsequent sterilization, while the microspheres, which carry the growth factors, are produced under aseptic conditions. The mixing of the coated granules and the microspheres is done just before the preparation of the biocompatible and biodegradable implant. The bonding is achieved in a gaseous $CO_2$ atmosphere at low temperatures of about 20° C. to about 37° C. and a pressure of about 20 bar to about 200 bar, preferably about 30 bar to about 40 bar. Under these conditions and at such low temperatures, the growth factors may be handled easily without the danger of degradation or alteration.

BRIEF DESCRIPTION OF THE DRAWINGS

Further advantages of the invention will become apparent from the description of exemplary embodiments of the invention in which.

DETAILED DESCRIPTION OF THE INVENTION

Figure 1:
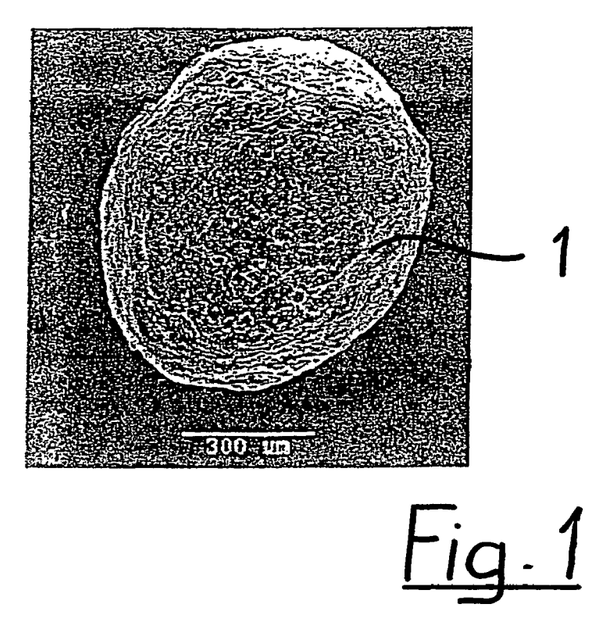
FIG. 1 is an electron microscope view of a biocompatible and biodegradable coated granule used for the fabrication of implants according to the invention.
Figure 2:
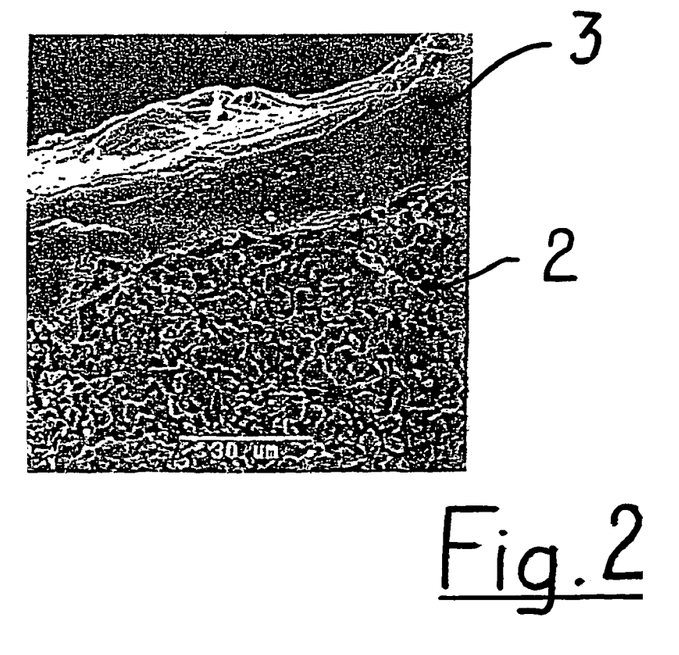
FIG. 2 is a detail of a cross-sectional view of the coated biocompatible and biodegradable granule and of FIG. 1 showing the homogeneous and thin coating of a microporous granule.

The coated granule 1 depicted in FIGS. 1 and 2 is of generally spherical shape. In spite of its usually relatively porous structure it has a very smooth outer surface due to being coated with a biocompatible and biodegradable polymer 3. The base 2 material in the shown embodiment is tricalcium phosphate (TCP). From FIG. 2, it is apparent that the granule 1 has a porous structure preferably comprising micropores having an average diameter of larger than 0 μm to about 10 μm, preferably about 0.1 μm to about 6 μm. It is to be noted that very densely sintered granules may have no microporosity at all. The coating 3 is a poly-lactide-co-glycolide (PLGA) and encloses the base material 2 completely like a shell. It has a thickness of about 2 μm to about 300 μm, preferably about 5 μm to about 20 μm.

Figure 3:
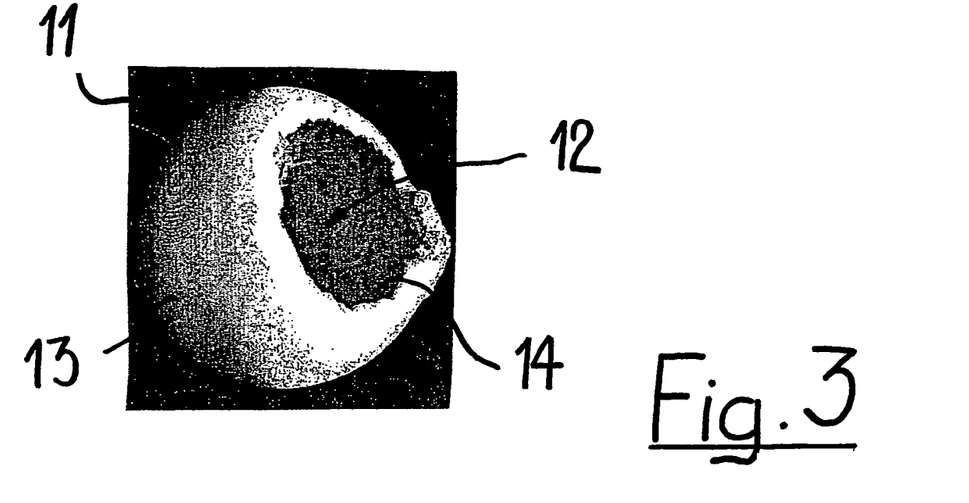
FIG. 3 is an electron microscope view of a hollow granule having a macroscopic opening in the granule wall.

FIG. 3 shows a hollow, generally spherical granule 11. The wall 13 of the granule 11 has an opening 14, which communicates with the cavity 12 of the granule. The hollow spherical granules 11 with an opening 14 in the granule wall 13 may be produced from slurry consisting of the biocompatible material water and an adhesive. Droplets of the slurry are brought onto a heated plate. The water in the slurry droplet boils and evaporates instantaneously out of the droplets leaving an evaporation crater in the droplet wall. When the droplets are cooled off hollow granules 11 having a macroscopic opening 14 in the granule wall 13 are formed. This granule may then be coated.

Figure 4:
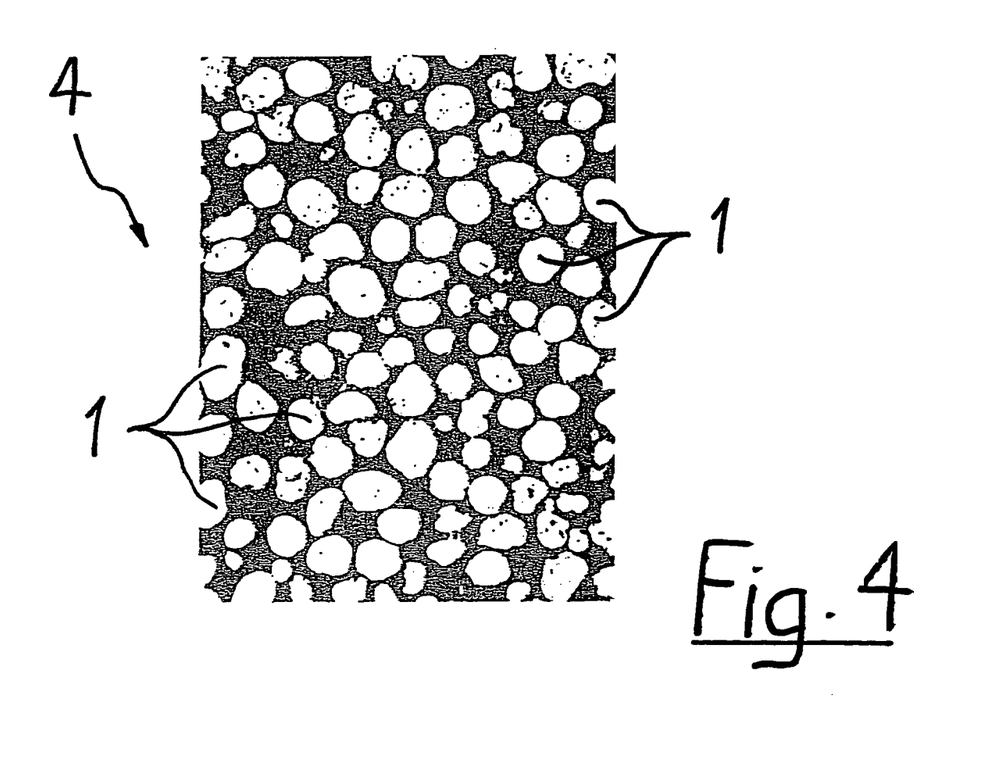
FIG. 4 is a light microscope cross-sectional view of a biocompatible and biodegradable implant made of a number of coated solid biocompatible and biodegradable granules demonstrating the interconnected and open porosity in between the granules.

FIG. 4 shows a light microscopy image of a cross-section of a TCP-PLGA implant 4 made of a number of granules 1 as depicted in FIGS. 1 and 2. The implant may also be formed of hollow granules, or of hollow granules 11 having an opening in the granule wall 13, as depicted in FIG. 3, or of mixtures thereof. The granules may all be coated or be only partly coated. The polymer coating cannot be observed at the shown magnification. The interconnected macroscopic porosity, however, can clearly be observed. The binary image of FIG. 4 is achieved after digitizing the image values, noise reduction and thresholding of the results. The granules 1 are fused with each other, the fusing having been achieved within a mold in a pressurized $CO_2$-atmosphere. The individual granules 1 are fused together only by linkage of the polymer-coatings of the granules. The shape of the individual granules 1 is basically spherical. The depicted implant 4 is made of biocompatible and biodegradable granules 1 of different sizes in the range of about 500 μm to about 800 μm, which results in an open interconnected structure with a good resistance to mechanical stress, such as, for example, pressure.

Granular Base Material:

Preferred biodegradable or bioresorbable materials include bioceramics such as calcium phosphates and calcium sulfates, bioglasses, and mixtures thereof. The calcium-based ceramics include, as monocalcium phosphate monohydrate (MCPM, $Ca(H_2PO_4)_2.H_2O$), monocalcium phosphate anhydrous (MCPA, $Ca(H_2PO_4)_2$), tetracalcium phosphate (TetCP, $Ca_4(PO_4)_2O$), calcium orthophosphate phosphate (OCP, $Ca_8H_2(PO_4)_6.5H_2O$), calcium pyrophosphate (CaP, $Ca_2P_2O_7$), dicalcium phosphate anhydrous (DCP, $CaHPO_4$), dicalcium phosphate dihydrate (DCPD, $CaHPO_4.2H_2O$), β-tricalcium phosphate (β-TCP, $Ca_3(PO_4)_2$), α-tricalcium phosphate (α-TCP, $Ca_3(PO_4)_2$), and apatite such as hydroxyapatite (HA, $Ca_{10}(PO_4)_6(OH)_2$). Calcium phosphate ceramics are known for their excellent biocompatibility and are therefore used in various biomedical applications, HA and TCP among them being the most used bioceramics in orthopedic and maxillo-facial applications and for the treatment of bone defects. Their dose ionic similarity with the mineral components of bone, their adjustable resorption kinetics to the need of a specific therapy and their bioactive properties have been mentioned before in the prior art. While HA is commonly considered to be non-biodegradable, some resorption behavior has been reported in in-vivo studies (Oonishi et al. 1999). β-TCP is generally considered to be biodegradable and is known to degrade faster than HA. After resorption of TCP in vivo new bone tissue is reported to replace the resorbed materials.

Preparation of β-TCP Granules

From β-TCP powder granules are prepared, for example, by a spheronization route. 70 g β-TCP powder (purum p.a. >96%, Fluka, CH) is mixed with 1 g dextin (Retalin Dextrin K51) in a mortar. 20 ml deionized water is slowly added to the powdery mixture under continuous stirring. The resultant paste is extruded through a multi-hole (φ: 800 μm) nozzle (Cyclo, Typ XYCG, Probst Technik, CH) and spheronized during ca. 3 min a pelletrounder (Probst Technik, CH) in order to obtain granules having an average diameter of about 350 μm to about 1000 μm. The obtained β-TCP granules with a diameter between 500 and 1000 μm are then calcinated and sintered at a temperature of 1150° C. during 4 hours in a furnace (Nabertherm, CH).

Other method such as high-shear mixer and fluidized bed granulation can also be used in order to produce rounded granules.

Biocompatible and Biodegradable Polymer-Coating

Meanwhile a large number of biocompatible and biodegradable or bioresorbable polymers are known from the prior art, among poly(α-hydroxyesters), poly(ortho esters), polyanhydrides, poly(phosphazenes), poly(propylene fumarate), poly(ester amides), poly(ethylene fumarate), polylactide, polyglycolide, polycaprolactone, poly(glycolide-co-trimethylene carbonate), polydioxanone, co-polymers thereof and blend of those polymers. By way of example only the invention will be illustrated with reference to poly-lactide-co-glycolide (PLGA), which is known for its biocompatibility and biodegradability. For this purpose, a solution of PLGA with a lactide to glycolide molar ratio of 50/50 (PLGA 50:50, Resomer RG503, Boehringer Ingelheim, D) in dichloromethan ($CH_2Cl_2$) is first prepared. The concentration of the polymer was about 0.1 g to 0.2 g PLGA 50:50 in 1 ml $CH_2Cl_2$. The β-TCP granules are immersed in the PLGA 50:50 solution. While the resultant mixture is constantly stirred, the solvent evaporates until a thin film of polymer is deposed on the surface of the β-TCP granules. Agglomerated granules can be then separated using a labor mixer and sieved. The extraction of the solvent is finally carried out for 36 h under vacuum (100 mbar).

A far more economic coating method, which results in a very homogenous coating of the β-TCP granules is the spray coating process in a fluidized bed machine (GPCG1, Glatt, D). For that purpose, 310 g pure β-TCP granules (500-710 μm) are placed on a perforated plate. While air flows through the plate, the granules are fluidized. A cylinder, which may be placed in the center above the perforated plate, canalizes the fluidized granules due to a flow gradient, which exists between the center of the plate and the circumference thereof. In this case, a spray nozzle is located underneath the cylinder in the center thereof. As the granules are fluidized and flow up the cylinder, they are coated with a 7.5% w/w PLGA 50:50 (Resomer RG503, Boehringer Ingelheim, D) in $CH_2CL_2$ solution. Due to the continuous circulation of the fluidized granules a very homogeneous coating is obtained. After spraying 570 g PLGA50:50 solution at a spraying rate of ca. 10 g/min, the coating process is stopped. With these coating parameters, granules can be obtained with a coating layer corresponding to about 6% of the total weight of the granules. The coated granules are then taken out of the fluidized bed machine and dried under vacuum (100 mbar) during at least 24 hours.

Using the same fluidized bed machine, it is also possible to coat β-TCP granules with PLGA85:15. (Resomer RG858, Boehringer Ingelheim, D). In one experiment, 493 g β-TCP granules (500-710 μm) were coated with ca. 1300 PLGA85: 15 in $CH_2Cl_2$ solution. At the end of the coating, coated granules with ca. 13% w/w PLGA85:15 could be obtained.

It is apparent for those skilled in the art that by selecting different coating solutions and varying the coating time, different layers of coatings having different thicknesses may be applied to the β-TCP granules. This includes the coating with biologically active substances as an individual coating or mixed or dissolved in the polymer coating.

Preparation of Biocompatible and Biodegradable Implants

β-TCP-PLGA biocompatible and biodegradable implants are prepared from β-TCP granules, which are coated with at least one layer of PLGA. Various methods for the fabrication of implants may be used in order to fuse the polymer-coated granules together, among them heat treatments, application of solvents, use of pressurized $CO_2$, chemical linkage, mechanical fusion by applying pressure, and mixtures of those methods.

By a fusion method, which applies a heat treatment at moderate temperatures the biocompatible and biodegradable implant may be prepared as follows:

700 mg PLGA 50:50 coated β-TCP granules are poured into a polysiloxane mold, having the desired shape, and heated to a temperature of about 75° C. to about 90° C. The granules are slightly compressed in the mold and kept at 75° C. to about 90° C. for at least about 10 seconds. Typically the process time amounts to about 10 seconds to about 5 minutes, preferably for about 1 minute to about 2 minutes. After that, the mold containing the fused granules is cooled down to ambient temperature. After cooling, the polymer coating hardens and the implant becomes stable enough to be removed from the mold and implanted.

The fusing of coated granules applying a method using pressurized $CO_2$ may be carried out as follows:

After filing a polysiloxane mold with a desired shape with 700 mg PLGA 50:50 coated β-TCP granules, the mold is place in a high pressure vessel at room temperature. After closure of the vessel, $CO_2$ is introduced into the vessel until a pressure of about 50 bar is reached. The pressure is increased at a ramp of about 2 bar per second. Once the maximum pressure is reached, it is held for at least about 3 seconds. Typically the pressure is held for about 3 seconds to about 180 seconds, preferably less than 30 seconds. Then, the $CO_2$ pressure is decreased at a rate of about 0.5 bar per second. As the $CO_2$ pressure in the vessel equilibrates with the outer atmospheric pressure, the vessel is opened and the mold is taken out. The implant made of the fused coated granules can then be extracted out of the mold. The whole process is preferably performed at room temperature or at slightly elevated temperatures of about 24° C. to about 37° C. Such an implant has a porosity of ca. 55% and a median pore diameter of ca. 280 µm.

Since the β-TCP granules are homogeneously coated with PLGA they are capable of fusing together during the $CO_2$ treatment. The $CO_2$ acts as a solvent for the coating. This results in a decrease of the glass transition temperature ($T_g$) of the polymer below the processing temperature. By the combination of the gas pressure and the reduction of $T_g$ the granules are able to fuse by polymer linkage only. Thus, it is apparent that homogenous coating of the granular base material is an essential prerequisite for the fusing of the coated granules. The implants comprise interstitial spaces in between the fused granules. The size of the interstitial spaces is depending on the thickness of the coating, on the compaction of the implant, and on the size of the coated granules. Thus, an application of moderate additional pressure on the mold cavity during the fusing of the granules reduces the interstitial space and allows a control thereof. An implant having larger interstitial spaces may be desirable in order to provide room for the in-growth of newly formed tissue.

Preparation of Biocompatible and Biodegradable Implants Loaded with Biologically Active Substances The processing using pressurized $CO_2$ for the fusing of the granules is preferred, because it permits to produce biocompatible and biodegradable implants including, for example, PLGA microspheres loaded with biologically active substances such as insulin like growth factor-1 (IGF-1).

The preparation of biocompatible and biodegradable implants loaded with IGF-1 could be carried out as follows:

25 mg PLGA50:50 microspheres (Resomer RG502H, Boehringer Ingelheim, D) loaded with IGF-1 were mixed in a polysiloxane mould with 950 mg of coated granules using a small spatula. The granules used for this experiment were coated with PLGA50:50 (Resomer RG502H, Boehringer Ingelheim, D) in order to achieve a material compatible interface between the granules and the microspheres. For a homogenous microsphere distribution through the scaffold, the polysiloxane mould filled with the biomaterials was vibrated with a vortex device (level 3, Vortex Genie 2, Bender & Hobein, CH) during 20 s. In order to prevent the segregation of the microspheres on the bottom of the mould, the mould was turned upside down and the vibrating was repeated. The consolidation of the implant was then achieved under pressurized $CO_2$ atmosphere at 30 bar during 60 s. After the consolidation step, the biocompatible and biodegradable implant loaded with IGF-1 could be extracted out from the mould and analyzed.

The release kinetics of IGF-1 was investigated for microspheres loaded with this biologically active substance and for implants containing such loaded microspheres and consolidated using the pressurized $CO_2$ technique. It appeared that after 1 day, the released amount of IGF-1 from the microspheres was ca. 40% and the released amount from the biocompatible and the biodegradable implant was ca. 13%. At day 7, the released amount of IGF-1 from the microspheres was ca. 100% and the amount from the implant was ca. 80%. After about 20 days, the amount of IGF-1 was totally released from the biocompatible and biodegradable implant. This demonstrates that such implants could be used as a drug delivery system for the treatment of bone defects.

In accordance with the invention there is described a biocompatible and biodegradable implant for a cavity in a bone of a living organism which is made of a biocompatible and biodegradable granules which are selected from the group consisting of biopolymers, bioglasses, bioceramics preferably calcium sulfate, calcium phosphate such as monocalcium phosphate monohydrate, monocalcium phosphate anhydrous, dicalcium phosphate dihydrate, dicalcium phosphate anhydrous, tetracalcium phosphate, calcium orthophosphate phosphate, α-tricalcium phosphate, β-tricalcium phosphate, apatite such as hydroxyapatite, or a mixture thereof. The biocompatible and biodegradable granules are provided with a coating, which comprises at least one layer of a biocompatible and biodegradable polymer which is selected from the group consisting of poly(α-hydroxyesters), poly(orthoesters), polyanhydrides, poly(phosphazenes), poly(propylene fumarate), poly(ester amides), poly(ethylene fumarate), polylactide, polyglycolide, polycaprolactone, poly(glycolide-co-trimethylene carbonate), polydioxanone, co-polymers thereof and blends of those polymers. The biocompatible and biodegradable implants are obtained by fusing together the polymer-coated granules through polymer-linkage of the polymer coatings of neighboring granules.

The invention claimed is:

1. Biocompatible and biodegradable implant for filling a cavity in a living organism comprising polymer-coated biocompatible and biodegradable granules fused together through polymer linkage, said granules being made of biocompatible and biodegradable materials selected from the group consisting of biopolymers, bioglasses, bioceramics and a mixture thereof, and said granules having an equivalent-diameter in a range from about 350 µm to about 2000 µm; a major portion of the surface area of said granules being coated with at least one biocompatible and biodegradable layer of a polymer selected from the group consisting of poly(α-hydroxyesters), poly(ortho esters), polyanhydrides, poly(phosphazenes), polypropylene fumarate), polyester amides), polyethylene fumarate), polylactide, polyglycolide, polycaprolactone, poly(glycolide-co-trimethylene carbonate), polydioxanone, co-polymers thereof and a blend of the polymers, and said polymer layer having a thickness in a range of 2 µm to 300 µm corresponding to a weight fraction of about 4% to about 15% of the weight of said implant, wherein the polymer linkage is carried out such that after fusing the granules together, an open interconnected porosity with macropores having an average diameter in a range of about 100 μm to about 500 μm, is achieved.

2. Biocompatible and biodegradable implant as in claim 1, wherein the bioceramic is calcium sulfate or calcium phosphate.

3. Biocompatible and biodegradable implant as in claim 2, wherein the calcium phosphate is selected from the group consisting of monocalcium phosphate monohydrate, monocalcium phosphate anhydrous, dicalcium phosphate dehydrate, dicalcium phosphate anhydrous, tetracalcium phosphate, calcium orthophosphate phosphate, calcium pyrophosphate, α-tricalcium phosphate, β-tricalcium phosphate, apatite, hydroxyapatite and a mixture thereof.

4. Biocompatible and biodegradable implant as in claim 1, wherein the equivalent-diameter of said granules is in the range of about 500 μm to about 1000 μm.

5. Biocompatible and biodegradable implant as in claim 1, wherein said granules are of a regular shape.

6. Biocompatible and biodegradable implant as in claim 5, wherein said regular shape is a spherical shape.

7. Biocompatible and biodegradable implant as in claim 1, wherein the thickness of the polymer layer is in the range of about 5 μm to about 20 μm.

8. Biocompatible and biodegradable implant as in claim 1, wherein the average diameter of the macropores is in the range of about 200 μm to about 300 μm.

9. Biocompatible and biodegradable implant as in claim 1, wherein the biocompatible and biodegradable granules are selected from the group consisting of solid granules, porous granules, hollow granules, hollow granules with at least one opening in the granule wall enclosing the interior hollow space, and mixtures thereof.

10. Biocompatible and biodegradable implant as in claim 9, wherein porous biocompatible and biodegradable granules are used.

11. Biocompatible and biodegradable implant as in claim 10, wherein the porous biocompatible and biodegradable granules include micropores having an average diameter in a range of more than 0 to about 10 μm.

12. Biocompatible and biodegradable implant as in claim 11, wherein the opening in the granule wall of the hollow granules is larger than the average diameter of the micropores in the porous granules.

13. Biocompatible and biodegradable implant as in claim 12, wherein the average diameter of the micropores is in the range of about 0.1 μm to about 6 μm.

14. Biocompatible and biodegradable implant as in claim 11, wherein the porous granules include macropores having an average diameter in a range of more than about 10 μm to about 500 μm.

15. Biocompatible and biodegradable implant as in claim 14, wherein the average diameter of the macropores is in the range of about 100 μm to about 300 μm.

16. Biocompatible and biodegradable implant as in claim 1, further comprising at least one biological active substance that is integrated into the granules and/or into the biocompatible and biodegradable coating, and/or forming a coating layer itself.

17. Biocompatible and biodegradable implant as in claim 1, wherein mixtures of non-coated and polymer-coated granules are fused together.

18. Biocompatible and biodegradable implant as in claim 1, wherein said biodegradable and biocompatible implant is made of two or more kinds of granules, said two or more kinds of granules being made of different biocompatible materials and/or comprising polymer-coatings that are distinct from each other and/or having different equivalent diameters.

19. Biocompatible and biodegradable implant as in claim 18, wherein the two or more kinds of granules are solid granules, porous granules, hollow granules, and/or hollow granules with at least one opening in the granule wall, or mixtures thereof, and said implant being shaped in a manner to accommodate the granules.

20. Biocompatible and biodegradable implant as in claim 1, wherein the granules are mixed with microspheres made of a biodegradable and biocompatible material and loaded with at least one biologically active substance.

21. Biocompatible and biodegradable implant as in claim 1, wherein said biocompatible and biodegradable granules are spray-coated with a biocompatible and biodegradable polymer to form a polymer coating.

22. Biocompatible and biodegradable implant as in claim 21, wherein said biocompatible and biodegradable granules are spray-coated in a fluidized bed machine.

23. Biocompatible and biodegradable implant as in claim 21, wherein the thickness of the polymer coating is in the range of about 5 μm to about 20 μm.

24. Biocompatible and biodegradable implant as in claim 1, wherein said granules are fused together in a mold in a pressurized $CO_2$ atmosphere under a pressure in a range of about 20 bar to about 200 bar, for at least about 3 seconds.

25. Biocompatible and biodegradable implant as in claim 24, wherein the pressure is about 50 bar.

26. Biocompatible and biodegradable implant as in claim 24, wherein the granules are under pressure for a range of about 3 seconds to about 180 seconds.

27. Biocompatible and biodegradable implant as in claim 1, wherein said granules are fused together by subjecting them within a mold to a heat treatment at a temperature in a range of about 70° C. to about 220° C. for at least about 10 seconds.

28. Biocompatible and biodegradable implant as in claim 27, wherein the temperature is in the range of about 75° C. to about 90° C.

29. Biocompatible and biodegradable implant as in claim 27, wherein the granules are heat treated for a range of about 10 seconds to about 5 minutes.

30. Biocompatible and biodegradable implant as in claim 1, wherein said granules are fused together in a mold in a pressurized $CO_2$ atmosphere under a pressure in a range of about 20 bar to about 200 bar for at least about 3 seconds, or said granules are fused together by subjecting them within a mold to a heat treatment at a temperature in a range of about 70° C. to about 220° C. for at least about 10 seconds.

31. Biocompatible and biodegradable implant as in claim 1, wherein the granules are entirely coated with the at least one biocompatible and biodegradable layer of a polymer.

* * * * *